(12) United States Patent
Assmann et al.

(10) Patent No.: US 6,359,142 B1
(45) Date of Patent: Mar. 19, 2002

(54) SULFONYL OXAZOLONES AND THEIR USE FOR COMBATING UNDESIRABLE MICROORGANISMS

(75) Inventors: Lutz Assmann, Langenfeld; Manfred Jautelat, Burscheid; Ulrike Wachendorff-Neumann, Neuwied; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/787,054

(22) PCT Filed: Sep. 9, 1999

(86) PCT No.: PCT/EP99/06650

§ 371 Date: Mar. 13, 2001

§ 102(e) Date: Mar. 13, 2001

(87) PCT Pub. No.: WO00/15620

PCT Pub. Date: Mar. 23, 2000

(30) Foreign Application Priority Data

Sep. 16, 1998 (DE) .......................................... 198 42 353

(51) Int. Cl.[7] .................... C07D 263/38; C07D 413/12; A01N 43/76
(52) U.S. Cl. ..................... 548/226; 548/236; 514/376
(58) Field of Search ................................ 548/226, 236; 514/376

(56) References Cited

U.S. PATENT DOCUMENTS

| 3,931,213 | A | * | 1/1976 | Kaminski et al. | 260/307 |
| 4,097,262 | A | * | 6/1978 | Cheng et al. | 71/90 |
| 4,957,933 | A | * | 9/1990 | Geffken et al. | 514/376 |
| 5,223,523 | A | * | 6/1993 | Adams, Jr. et al. | 514/376 |
| 5,883,250 | A | * | 3/1999 | Kruger et al. | 540/544 |

FOREIGN PATENT DOCUMENTS

| DE | 196 09 060 | 2/1997 |
| DE | 196 23 207 | 12/1997 |
| DE | 196 42 865 | 4/1998 |

OTHER PUBLICATIONS

Zh. Org. Khim, 27 (month unavailable) 1991, pp. 1262–1270.

* cited by examiner

Primary Examiner—Floyd D. Higel
Assistant Examiner—Kamal Saeed
(74) Attorney, Agent, or Firm—Joseph C. Gil; Raymond J. Harmuth

(57) ABSTRACT

Novel sulphonyloxazolones of the formula (I)

in which $R^1$ represents alkyl or represents optionally substituted heterocyclyl or represents a radical of the formula in which $R^3$ represents halogen, alkyl or phenyl, $R^4$ represents hydrogen or alkyl and $R^5$ represents alkyl or optionally substituted phenyl, and $R^2$ represents alkyl, a process for preparing these substances and their use for controlling undesirable microorganisms.

Novel intermediates of the formula (II)

and a process for their preparation.

7 Claims, No Drawings

SULFONYL OXAZOLONES AND THEIR USE FOR COMBATING UNDESIRABLE MICROORGANISMS

This application is a 371 of PCT/EP99/06650 filed on Sep. 9, 1999.

The present invention relates to novel sulphonyloxazolones, to a process for their preparation and to the use for controlling undesirable microorganisms.

Certain sulphonyloxazolones, such as, for example, 4-[(4-chlorophenyl)sulphonyl]-3-(2,4,6-trimethyl-phenyl)-1,2,4-oxadiazol-5(4H)-one, have already been disclosed (cf. Zh. Org. Khim. 27 (1991), 1262–1270). However, a biological action of these compounds has hitherto not been described.

Novel sulphonyloxazolones of the formula

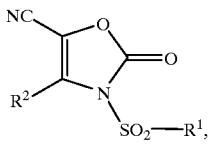
(I)

in which
R$^1$ represents alkyl or represents optionally substituted heterocyclyl or represents a radical of the formula

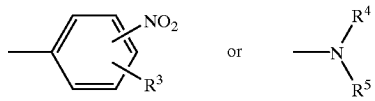

in which
R$^3$ represents halogen, alkyl or phenyl,
R$^4$ represents hydrogen or alkyl and
R$^5$ represents alkyl or optionally substituted phenyl, and
R$^2$ represents alkyl,
have now been found.

Furthermore, it has been found that sulphonyloxazolones of the formula (I) are obtained, when oxazolones of the formula

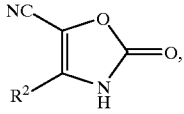
(II)

in which
R$^2$ is as defined above,
are reacted with sulphonyl halides of the formula R$^1$—SO$_2$—Hal (III)

in which
R$^1$ is as defined above and
Hal represents chlorine or bromine,
if appropriate in the presence of an acid binder and if appropriate in the presence of a diluent.

Finally, it has been found that the sulphonyloxazolones of the formula (I) have very good microbicidal properties and can be used for controlling undesirable micro-organisms in crop protection and in agriculture.

Surprisingly, the sulphonyloxazolones of the formula (I) according to the invention have better activity against undesirable microorganisms, in particular against fungi, than the constitutionally most similar prior-art substances of the same direction of action.

The formula (I) provides a general definition of the substances according to the invention.

R$^1$ preferably represents alkyl having 1 to 4 carbon atoms or represents a heterocyclyl radical having 5 or 6 ring members and 1 to 3 heteroatoms, such as nitrogen, oxygen and/or sulphur, where this radical may contain a keto or imino group and may be mono- to trisubstituted by identical or different substituents from the group consisting of halogen, cyano, nitro, amino, hydroxyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkylcarbonyl having 1 to 4 carbon atoms in the alkyl moiety, alkoxycarbonyl having 1 to 3 carbon atoms in the alkoxy moiety, carbamoyl, alkylaminocarbonyl having 1 to 4 carbon atoms in the alkyl moiety, dialkylaminocarbonyl having 1 to 4 carbon atoms in the individual alkyl moieties, hydroximinoalkyl or alkoximinoalkyl having in each case 1 to 4 carbon atoms in the individual alkyl moieties and cycloalkyl having 3 to 6 carbon atoms.

R$^1$ furthermore preferably represents a radical of the formula

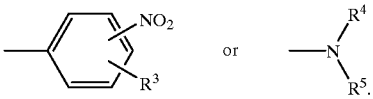

R$^3$ preferably represents fluorine, chlorine, bromine, alkyl having 1 to 6 carbon atoms or represents phenyl.
R$^4$ preferably represents hydrogen or alkyl having 1 to 6 carbon atoms.
R$^5$ preferably represents alkyl having 1 to 6 carbon atoms or represents phenyl which may be mono- to trisubstituted by identical or different substituents from the group consisting of halogen, nitro, C$_1$–C$_6$-alkyl, C$_1$–C$_6$-alkoxy, C$_1$–C$_6$-alkylthio, C$_1$–C$_6$-halogenoalkyl having 1 to 5 identical or different halogen atoms, C$_1$–C$_6$-halogenoalkoxy having 1 to 5 identical or different halogen atoms, C$_1$–C$_6$-halogenoalkylthio having 1 to 5 identical or different halogen atoms, cyano and cycloalkyl having 3 to 6 carbon atoms.

R$^2$ preferably represents alkyl having 1 to 6 carbon atoms.

R$^1$ particularly preferably represents methyl, ethyl, propyl, isopropyl or represents furyl, thienyl, oxazolyl, isoxazolyl, pyrazolyl, imidazolyl, thiazolyl, isothiazolyl, oxadiazolyl, thiadiazolyl, pyridinyl, pyrimidinyl, pyridazinyl, pyrazinyl, 1,2,3-triazinyl, 1,2,4-triazinyl, 1,3,5-triazinyl, pyrrolidinyl, piperidinyl or morpholinyl, where these radicals may be mono-, di- or trisubstituted by identical or different substituents from the group consisting of fluorine, chlorine, bromine, cyano, nitro, amino, hydroxyl, carbamoyl, methyl, ethyl, n- or i-propyl, n-, i-, s- or t-butyl, cyclopropyl, methoxy, ethoxy, n- or i-propoxy, trifluoromethyl, trifluoroethyl, difluoromethoxy, trifluoromethoxy, acetyl, propionyl, methoxycarbonyl, ethoxycarbonyl, hydroxyiminomethyl, hydroximinoethyl, methoximinomethyl, ethoximinomethyl, methoximinoethyl and ethoximinoethyl.

$R^1$ furthermore particularly preferably represents a radical of the formula

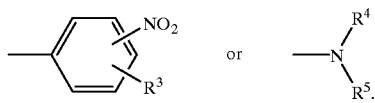

$R^3$ particularly preferably represents fluorine, chlorine, bromine, methyl, ethyl, n-propyl, isopropyl, n-butyl, sec-butyl, iso-butyl, tert-butyl or phenyl.

$R^4$ particularly preferably represents hydrogen, methyl, ethyl, n-propyl, isopropyl, n-butyl, sec-butyl, iso-butyl or tert-butyl.

$R^5$ particularly preferably represents methyl, ethyl, n-propyl, isopropyl, n-butyl, sec-butyl, iso-butyl or tert.-butyl, or represents phenyl which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-pro pylthio, trifluoromethyl, trifluoroethyl, difluoromethoxy, trifluoromethoxy, difluorochloromethoxy, trifluoroethoxy, cyano, cyclopropyl, cyclopentyl and cyclohexyl.

$R^2$ particularly preferably represents methyl, ethyl, n-propyl, isopropyl, n-butyl, sec-butyl, iso-butyl or tert-butyl.

$R^1$ very particularly preferably represents methyl, ethyl, isopropyl or represents furyl, thienyl, oxazolyl, isoxazolyl, pyrazolyl, imidazolyl, thiazolyl, isothiazolyl, oxadiazolyl, thiadiazolyl, pyridinyl, pyrimidinyl, 1,2,4-triazinyl, pyrrolidinyl, piperidinyl or morpholinyl, where these radicals may be mono-, di- or trisubstituted by identical or different substituents from the group consisting of fluorine, chlorine, bromine, cyano, nitro, amino, hydroxyl, carbamoyl, methyl, ethyl, n- or i-propyl, cyclopropyl, methoxy, ethoxy, tri-fluoromethyl, difluoromethoxy, trifluoromethoxy, acetyl, methoxycarbonyl, ethoxycarbonyl, hydroxyiminomethyl, hydroxyiminoethyl, methoximino-methyl, ethoxyiminomethyl, methoximinoethyl and ethoximinoethyl.

$R^1$ furthermore very particularly preferably represents a radical of the formula

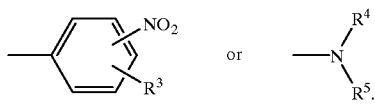

$R^3$ very particularly preferably represents fluorine, chlorine, bromine, methyl, ethyl, n-propyl, isopropyl, n-butyl, tert-butyl or phenyl.

$R^4$ very particularly preferably represents hydrogen, methyl, ethyl, n-propyl, isopropyl or n-butyl.

$R^5$ very particularly preferably represents methyl, ethyl, n-propyl, isopropyl, n-butyl, sec-butyl, iso-butyl or tert-butyl, or represents phenyl which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, methylthio, trifluoromethyl, trifluoro-ethyl, difluoromethoxy, trifluoromethoxy, difluorochloromethoxy, trifluoroethoxy, cyano, cyclopropyl, cyclopentyl and cyclohexyl.

$R^2$ also very particularly preferably represents methyl, ethyl, n-propyl, isopropyl, n-butyl, sec-butyl, iso-butyl or tert-butyl.

The meanings of the substituents given above can be combined with one another as desired Moreover, individual definitions may not be applicable.

Using 5-cyano4-ethyl-3H-[1,3)-oxazol-2-one and 3,5-dimethylisoxazole-4-sulphonyl chloride as starting materials, the course of the process according to the invention can be illustrated by the equation below.

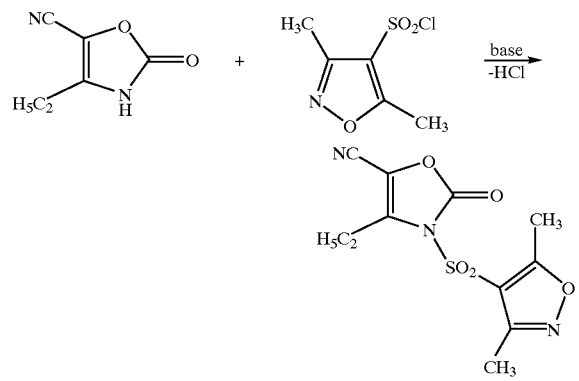

The formula (II) provides a general definition of the oxazolones required as starting materials for carrying out the process according to the invention. In this formula, $R^2$ preferably has those meanings which have already been mentioned in connection with the description of the substances of the formula (I) according to the invention as being preferred for this radical.

The oxazolones of the formula (II) have hitherto not been known. They can be prepared by reacting, in a first step, hydroxyketones of the formula (IV)

in which
$R^2$ is as defined above,
with urea in the presence of glacial acetic acid and reacting, in a second step, tie resulting products with phosphorus oxychloride.

The formula (IV) provides a general definition of the hydroxyketones required as starting materials for carrying out this process. In this formula, $R^2$ preferably has those meanings which have already been mentioned in connection with the description of the substances of the formula (I) according to the invention as being preferred for this radical.

The hydroxyketones of the formula (IV) are known or can be prepared by known methods.

When carrying out the above process for preparing oxazolones of the formula (II), the reaction temperatures can be varied within a relatively wide range. In general, the first step is carried out at temperatures between 10° C. and 160° C,. preferably between 20° C. and 140° C. The second step is generally carried out at temperatures between 10° C. and 100° C,. preferably between 20° C. and 80° C.

In the preparation of oxazolones of the formula (II) by the above process, both the first step and the second step are generally carried out under atmospheric pressure. However, it is also possible to operate under increased pressure.

In the synthesis of oxazolones of the formula (II), the first step is generally carried out using, in the presence of glacial acetic acid, 1.5 to 3 mol of urea per mole of hydroxyketone of the formula (IV). Work-up is carried out by customary methods. In general, the reaction mixture is concentrated, the residue that remains is filtered through an adsorbent material, the residue obtained after concentration of the eluate is stirred with water and the resulting precipitate is filtered off with suction and dried. In the second step of the process, the intermediate is reacted with an excess of phosphorus oxychloride. Work-up is carried out by customary methods. In general, the reaction mixture is filtered off with suction through an adsorbent material, the filtrate is added to water, the resulting mixture is extracted with an organic solvent which is sparingly soluble in water and the combined organic phases are dried and concentrated under reduced pressure.

The formula (III) provides a general definition of the sulphonyl halides required as reaction components for carrying out the process according to the invention. In this formula, $R^1$ preferably has that meaning which has already been given in connection with the description of the compounds of the formula (I) according to the invention as being preferred for $R^1$. X preferably represents chlorine.

The sulphonyl halides of the formula (E) are known or can be prepared by known processes (cf. J. Heterocyclic Chem. 1981, 997–1006 and EP-A 0 238 824).

Suitable diluents for carrying out the process according to the invention are all inert organic solvents. Preference is given to using aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; esters such as methyl acetate or ethyl acetate.

Suitable acid binders for carrying out the process according to the invention are all customary inorganic or organic bases. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, furthermore ammonium compounds, such as ammonium hydroxide, ammonium acetate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process according to the invention, the reaction temperatures can be varied within a relatively wide range. In general, the process is carried out at temperatures between 0° C. and 150° C,. preferably between 20° C. and 120° C.

The process according to the invention is generally carried out under atmospheric pressure. However, it is also possible to operate under elevated or reduced pressure—in general between 0.1 bar and 10 bar.

For carrying out the process according to the invention, in general from 1 to 2 mol, preferably from 1 to 1.3 mol, of sulphonyl halide of the formula (III) and, if appropriate, from 1.0 to 2.0 mol, preferably from 1.0 to 1.3 mol, of acid acceptor are employed per mole of oxazolone of the formula (II).

Work-up is carried out by customary methods. In general, the reaction mixture is poured into water, the resulting mixture is extracted repeatedly with an organic solvent which is sparingly soluble in water, and the combined organic phases are dried and concentrated under reduced pressure. The residue that remains can, if appropriate, be freed of any impurities which are still present, using customary purification methods.

The compounds according to the invention have potent microbicidal activity and can be employed for controlling undesirable microorganisms, such as fungi and bacteria, in crop protection and in the protection of materials.

Fungicides can be employed [lacuna] crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus*;

Puccinia species, such as, for example, *Puccinia recondita*;

Sclerotinia species, such as, for example, *Sclerotinia sclerotiorum*;

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Alternaria species, such as, for example, *Alternaria brassicae*;

Pseudocercosporella species, such as, for example, *Pseudocercosporella herpotrichoides*.

The fact that the active compounds are well tolerated by plants at the concentrations required for controlling plant diseases permits the treatment of above-ground parts of plants, of propagation stock and seeds, and of the soil.

The active compounds according to the invention can be employed particularly successfully for controlling diseases in viticulture, fruit and vegetable growing, such as, for example, against Phytophthora species.

The active compounds according to the invention may also be employed to increase the yield of crops. Moreover, they have reduced toxicity and are tolerated well by plants.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:

Alternaria, such as *Alternaria tenuis*,
Aspergillus, such as *Aspergillus niger*.
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*, and
Staphylococcus, such as *Staphylococcus aureus*.

Depending on their particular physical and/or chemical properties, the active compounds can be converted to the customary formulations, such as solutions, emulsions, suspensions, powders, foams, pastes, granules, aerosols and micro-encapsulations in polymeric substances and in coating compositions for seeds, and ULV cool and warm fogging formulations.

These formulations are produced in a known manner, for example by mixing the active compounds with extenders, that is liquid solvents, liquefied gases under pressure and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are, for example, ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are, for example, crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are, for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are, for example, lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations, also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, bendicar, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), quinboxyfen, sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflurnizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1 H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl) ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1, 2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-)-methyl4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d] pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methaneamine,
8-hydroxyquinoline sulphate,
9H-xanthene-2-[(phenylamino)-carbonyl]-9-carboxylic hydrazide,
bis-(1-methylethyl)-3-methyl-4-((3-methylbenzoyl)oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methaneimidamide,
N-formyl-N-hydroxy-DL-alanine sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one, Bactericides:
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin, *Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, Metharhizium anisopliae, *Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M, *Paecilomyces fumosoroseus*, parathion A, parathion M, permethrin, phenthoate, phorate, phosalone, phosmet, phosphamidon, phoxim, pirimicarb, pirimiphos A, pirimiphos M, profenophos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thet a-cypernethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii,*
YI 5302,
zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[(2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides or fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the application rates of active compound are generally between 0.1 and 10,000 g/ha, preferably between 10 and 1000 g/ha. In the treatment of seed, the application rates of active compound are gen- erally between 0.001 and 50 g per kilogram of seed, preferably between 0.01 and 10 g per kilogram of seed. In the treatment of the soil, the application rates of active compound are generally between 0.1 and 10,000 g/ha, preferably between 1 and 5000 g/ha.

The compositions used for protecting industrial materials generally comprise the active compounds in an amount of from 1 to 95% by weight, preferably from 10 to 75% by weight.

The use concentrations of the active compounds according to the invention depend on the nature and the occurrence of the microorganisms to be controlled and on the composition of the material to be protected. The optimum application rate can be determined by test series. In general, the use concentrations are in the range of from 0.001 to 5% by weight, preferably from 0.05 to 1.0% by weight, based on the material to be protected.

The activity and the activity spectrum of the active compounds to be used according to the invention in the protection of materials, or of the compositions, concentrations or quite generally formulations prepared therefrom, can be increased by adding, if appropriate, other antimicrobially active compounds, fungicides, bactericides, herbicides, insecticides or other active compounds to widen the activity spectrum or to obtain particular effects, such as, for example, additional protection against insects. These compounds can have a broader spectrum of action than the compounds of the invention.

The preparation and the use of active compounds according to the invention are illustrated by the examples below.

PREPARATION EXAMPLES

Example 1

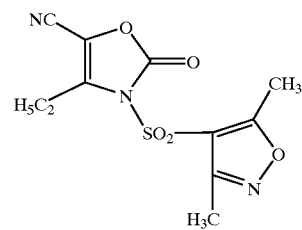

At room temperature, a solution of 2.8 g (20 mmol) of 5-cyano-4ethyl-3H-[1,3]-oxazol-2-one in 50 ml of tetrahydrofuran is admixed with stirring with 0.8 g (20 mmol) of sodium hydride (60%) in oil, and the mixture is then stirred at room temperature for 10 minutes. 4.0 g (20 mmol) of 3,5-dimethyl-isoxazole4-sulphonyl chloride are then added, and the mixture is stirred at room temperature for another 20 hours. For work-up, the reaction mixture is poured into 200 ml of water. The resulting mixture is extracted three times with in each case 50 ml of ethyl acetate. The combined organic phases are dried over sodium sulphate and concentrated under reduced pressure. The residue that remains is chromatographed over silica gel using the mobile phase methylene chloride. This gives 0.9 g (16% of theory) of 5-cyano4-ethyl-3-(3,5-dimethyl-isoxazole-4-sulphonyl)-3H-[1,3]-oxazol-2-one in the form of a colourless solid substance of melting point 117 to 122° C. log p:2.87

Preparation of Starting Materials

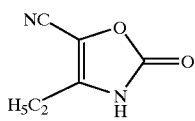
(II-1)

First Reaction Step

At room temperature, 8.8 g (0.1 mol) of 1-hydroxy-2-butanone are added with stirring to a mixture of 10.2 g (0.17 mol) of urea and 30 ml of glacial acetic acid. The mixture is heated under reflux for 4 hours and then concentrated under reduced pressure. The product that remains is chromatographed over silica gel using initially diethyl ether and then methanol as mobile phase. The residue that remains after concentration of the methanol fraction is stirred with 100 ml of water. The resulting precipitate is filtered off with suction and dried. This gives 3.9 g of a colourless solid substance of melting point 160 to 170° C.

Second Reaction Step

At room temperature, 30 g of the product prepared after the first reaction step are introduced with stirring into 150 ml of phosphorus oxychloride, the temperature of the mixture increasing to 50° C. The reaction mixture is heated under reflux for 20 hours and then, at room temperature, filtered off with suction through kieselguhr. The filtrate is concentrated under reduced pressure and the product that remains is, with cooling, added to 300 ml of water. The resulting mixture is extracted twice with in each case 80 ml of ethyl acetate. The combined organic phases are dried over sodium sulphate and then concentrated under reduced pressure. This gives 2.2 g of a product which, according to gas chromatogram, comprises 81% of 5-cycano-4-ethyl-3H-[1,3]-oxazol-2-one. Accordingly, the calculated yield is 5% of theory. log p:0.88

The substances of the formula (I) listed in Table 1 below are likewise prepared by the method described above.

TABLE 1

(I)

| Example No. | R² | R¹ | Melting point in ° C. |
|---|---|---|---|
| 2 | —CH₃ | (isoxazole with H₃C, CH₃) | 128–132 |
| 3 | —C₂H₅ | (thiophene with Cl, Cl) | 103–106 |

USE EXAMPLES

Example A

Phytophthora test (tomato)/protective
Solvent: 47 parts by weight of acetone
Emulsifier: 3 parts by weight of alkyl-aryl polyglycol ether To produce a suitable preparation of active compound, 1 part by weight of active compound is mixed with the stated amounts of solvent and emulsifier, and the concentrate is diluted to the desired concentration.

To test for protective activity, young plants are sprayed with the preparation of active compound at the stated application rate. After the spray coating has dried on, the plants are inoculated with an aqueous spore suspension of Phytophthora infestans. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection is observed.

Active compounds, application rates and test results are shown in the table below.

TABLE A

Phytophthora test (tomato)/protective

| Active compound | Active compound application rate in g/ha | Efficacy in % |
|---|---|---|
| According to the invention: | | |
| (1) | 50 | 94 |
| (2) | 50 | 100 |

Example B

Plasmopara test (grapevine)/protective
Solvent: 47 parts by weight of acetone
Emulsifier: 3 parts by weight of alkyl-aryl polyglycol ether To produce a suitable preparation of active compound, 1 part by weight of active compound is mixed with the stated amounts of solvent and emulsifier, and the concentrate is diluted to the desired concentration.

To test for protective activity, young plants are sprayed with the preparation of active compound at the stated application rate. After the spray coating has dried on, the plants are inoculated with an aqueous spore suspension of Plasmopara viticola and then remain in an incubation cabin at about 20° C. and 100% relative atmospheric humidity for 1 day. The plants are then placed in a greenhouse at about 21° C. and about 90% atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

Active compounds, application rates and test results are shown in the table below.

TABLE B

| Plasmopara test (grapevine)/protective | | |
|---|---|---|
| Active compound | Active compound application rate in g/ha | Efficacy in % |
| According to the invention: | | |
| 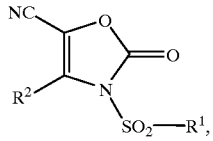 (2) | 50 | 96 |

What is claimed is:

1. A sulphonyloxazolone of the formula

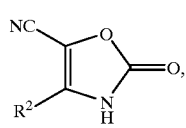 (I)

in which

R$^1$ represents alkyl having 1 to 4 carbon atoms or represents a heterocyclyl radical having 5 or 6 ring members and 1 to 3 heteroatoms, where this radical may contain a keto or imino group and may be mono-to trisubstituted by identical or different substituents from the group consisting of halogen, cyano, nitro, amino, hydroxyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkylcarbonyl having 1 to 4 carbon atoms in the alkyl moiety, alkoxycarbonyl having 1 to 3 carbon atoms in the alkoxy moiety, carbamoyl, alkylaminocarbonyl having 1 to 4 carbon atoms in the alkyl moiety, dialkylaminocarbonyl having 1 to 4 carbon atoms in the individual alkyl moieties, hydroximinoalkyl or alkoximinoalkyl having in each case 1 to 4 carbon atoms in the individual alkyl moieties and cycloalkyl having 3 to 6 carbon atoms, or represents a radical of the formula

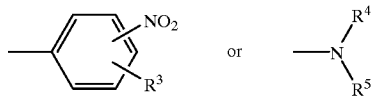

in which

R$^3$ represents fluorine, chlorine, bromine, alkyl having 1 to 6 carbon atoms or represents phenyl, R$^4$ represents hydrogen or alkyl having 1 to 6 carbon atoms, and R$^5$ represents alkyl having 1 to 6 carbon atoms or represents phenyl which may be mono-to trisubstituted by identical or different substituents from the group consisting of halogen, nitro, C1–C6-alkyl, C1–C6-alkoxy, C1–C6-alkylthio, C1–C6-halogenoalkyl having 1 to 5 identical or different halogen atoms, C1–C6-halogenoalkoxy having 1 to 5 identical or different halogen atoms, C1–C6-halogenoalkylthio having 1 to 5 identical or different halogen atoms, cyano and cycloalkyl having 3 to 6 carbon atoms, and R$^2$ represents alkyl having 1 to 6 carbon atoms.

2. A process for preparing a sulphonyloxazolone of the formula (I) according to claim 1, comprising the step of reacting an oxazolone of the formula

 (II)

in which

R$^2$ is as defined in claim 1, with a sulphonyl halide of the formula

R$^1$-SO$_2$-Hal (III)

in which

R$^1$ is as defined in claim 1 and

Hal represents chlorine or bromine.

3. A composition for controlling undesirable microorganisms, wherein said composition comprises a microbicidally effective amount of a sulphonyloxazolone of the formula (I) according to claim 1 in admixture with an inert diluent.

4. A method for controlling undesirable microorganisms, which method comprises the step of applying a microbicidally effective amount of a sulphonyloxazolone of the formula (I) according to claim 1 to said microorganisms or to their habitat.

5. A sulphonyloxazolone according to claim 1, wherein the formula of said sulphonyloxazolone is

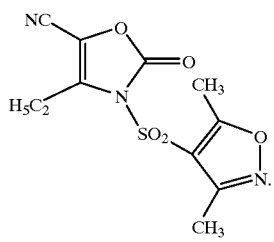

6. A sulphonyloxazolone according to claim 1, wherein the formula of said sulphonyloxazolone is

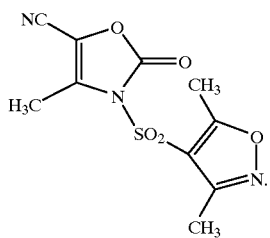

7. A sulphonyloxazolone of the formula (I) according to claim 1 wherein $R^1$ represents methyl, ethyl, isopropyl, or represents furyl, theinyl, oxazolyl, isoxazolyl, pyrazolyl; imidazolyl, thiazolyl, isothiazolyl, oxadiazolyl, thiadiazolyl, pyridinyl, pyrimidinyl, 1,2,4-triazinyl, pyrrolidinyl, piperidinyl or morpholinyl, where these radicals may be mono-, di-or trisubstituted by identical or different substituents, from the group consisting of fluorine, chlorine, bromine, cyano, nitro, amino, hydroxyl, carbamoyl, methyl, ethyl, n-or i-propyl, cyclopropyl, methoxy, ethoxy, trifluoromethyl, difluoromethoxy, trifluoromethoxy, acetyl, methoxycarbonyl, ethoxycarbonyl, hydroxyiminomethyl, hydroxyiminoethyl, methoximinomethyl, ethoxyiminomethyl, methoximinomethyl, and ethoximinoethyl, and $R^2$ represents methyl, ethyl, n-propyl, isopropyl, n-butyl, sec-butyl, iso-butyl or tert-butyl.

* * * * *